US011246472B2

(12) United States Patent
Takahashi et al.

(10) Patent No.: US 11,246,472 B2
(45) Date of Patent: Feb. 15, 2022

(54) ENDOSCOPE SYSTEM

(71) Applicant: FUJIFILM Corporation, Tokyo (JP)

(72) Inventors: Nobuharu Takahashi, Kanagawa (JP); Motohiko Matsushita, Kanagawa (JP); Takuro Ide, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/988,709

(22) Filed: Jan. 5, 2016

(65) Prior Publication Data

US 2016/0227982 A1    Aug. 11, 2016

(30) Foreign Application Priority Data

Feb. 5, 2015    (JP) .............................. JP2015-021096

(51) Int. Cl.
*A61B 1/00*    (2006.01)
*A61B 1/005*   (2006.01)
*A61B 1/31*    (2006.01)

(52) U.S. Cl.
CPC .......... *A61B 1/00078* (2013.01); *A61B 1/005* (2013.01); *A61B 1/0051* (2013.01);
(Continued)

(58) Field of Classification Search
CPC ............ A61B 1/00071; A61B 1/00078; A61B 1/00135; A61B 1/00142; A61B 1/00154;
(Continued)

(56) References Cited

U.S. PATENT DOCUMENTS 5,885,208 A * 3/1999 Moriyama ......... A61B 1/00078
                                                   600/144
5,941,815 A * 8/1999 Chang ..................... A61B 1/31
                                                   600/114
(Continued)

FOREIGN PATENT DOCUMENTS

JP    S55-112505    8/1980
JP    H08-201705    8/1996
(Continued)

OTHER PUBLICATIONS

"Office Action of China Counterpart Application", with English translation, dated Sep. 5, 2018, p. 1-p. 13.
(Continued)

*Primary Examiner* — Ryan N Henderson
(74) *Attorney, Agent, or Firm* — JCIPRNET

(57) ABSTRACT

There is provided an endoscope system which can secure appropriate bending stiffness of an insertion portion while maintaining the slide length of an endoscope insertion portion. According to one aspect of one of the present invention, in an endoscope system including an endoscope and an insertion assisting tool in which the endoscope is inserted and which assists the insertion of an endoscope insertion portion into a body, a flexible portion of the endoscope insertion portion includes a projection region which projects from the distal end opening of a tube body when the endoscope insertion portion is located in the distal end position in a movable range with respect to the tube body of the insertion assisting tool, and the projection region includes a bending stiffness change portion in which bending stiffness increases from a first position on the distal end side to a second position on the proximal end side.

10 Claims, 11 Drawing Sheets

(52) U.S. Cl.
CPC ...... *A61B 1/00071* (2013.01); *A61B 1/00082* (2013.01); *A61B 1/00154* (2013.01); *A61B 1/31* (2013.01)

(58) Field of Classification Search
CPC . A61B 1/00151; A61B 1/00156; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/0125; A61B 1/273; A61B 1/2733; A61B 1/2736; A61B 1/31; A61M 25/0102
USPC ........ 600/104, 106, 107, 114, 115, 139–152; 604/523–528
See application file for complete search history.

(56) References Cited

U.S. PATENT DOCUMENTS

| | | | | |
|---|---|---|---|---|
| 6,572,538 B2* | 6/2003 | Takase | ............ | A61B 1/005 600/139 |
| 6,860,849 B2* | 3/2005 | Matsushita | ........ | A61B 1/00071 600/140 |
| 7,041,052 B2* | 5/2006 | Saadat | ............ | A61B 1/0008 600/114 |
| 7,481,793 B2* | 1/2009 | Abrams | ............ | A61M 25/0662 604/164.01 |
| 7,537,562 B2* | 5/2009 | Takano | ............ | A61B 1/00082 600/114 |
| 7,713,191 B2* | 5/2010 | Sekiguchi | ........ | A61B 1/00055 600/116 |
| 7,833,150 B2* | 11/2010 | Yamamoto | ............ | A61B 90/57 600/102 |
| 7,909,755 B2* | 3/2011 | Itoi | ............ | A61B 1/00006 600/153 |
| 7,955,253 B2* | 6/2011 | Ewers | ............ | A61B 1/00149 600/114 |
| 8,012,084 B2* | 9/2011 | Machida | ............ | A61B 1/00082 600/115 |
| 8,083,670 B2* | 12/2011 | Ikeda | ............ | A61B 1/12 600/116 |
| 8,088,063 B2* | 1/2012 | Fujikura | ............ | A61B 17/3415 600/114 |
| 8,092,372 B2* | 1/2012 | Machida | ............ | A61B 1/00082 600/116 |
| 8,128,614 B2* | 3/2012 | Abrams | ............ | A61M 25/0662 604/528 |
| 8,216,128 B2 | 7/2012 | Matsuura et al. | | |
| 8,221,308 B2* | 7/2012 | Noguchi | ............ | A61M 25/01 600/117 |
| 8,366,606 B2* | 2/2013 | Watanabe | ............ | A61B 1/00071 600/144 |
| 8,439,825 B2* | 5/2013 | Sekiguchi | ........ | A61B 1/00039 600/116 |
| 8,579,802 B2* | 11/2013 | Robertson | ........ | A61B 1/00078 600/144 |
| 9,345,390 B2 | 5/2016 | Matsuo | | |
| 9,629,535 B2* | 4/2017 | Lal | ............ | A61B 1/31 |
| 2002/0002323 A1* | 1/2002 | Moriyama | ........ | A61B 1/00071 600/140 |
| 2002/0010386 A1* | 1/2002 | Matsushita | ........ | A61B 1/00071 600/140 |
| 2002/0013512 A1* | 1/2002 | Sendai | ............ | A61B 1/043 600/160 |
| 2002/0032368 A1* | 3/2002 | Takase | ............ | A61B 1/005 600/139 |
| 2002/0161281 A1* | 10/2002 | Jaffe | ............ | A61B 5/065 600/114 |
| 2003/0233025 A1* | 12/2003 | Saadat | ............ | A61B 1/0008 600/114 |
| 2004/0080613 A1* | 4/2004 | Moriyama | ........ | A61B 1/00078 348/65 |
| 2004/0186349 A1* | 9/2004 | Ewers | ............ | A61B 1/00082 600/114 |
| 2004/0186350 A1* | 9/2004 | Brenneman | ........ | A61B 1/0058 600/146 |
| 2005/0059861 A1* | 3/2005 | Nishiie | ............ | A61B 1/00071 600/144 |
| 2005/0124856 A1* | 6/2005 | Fujikura | ............ | A61B 17/3415 600/115 |
| 2005/0131343 A1* | 6/2005 | Abrams | ............ | A61M 25/0662 604/95.04 |
| 2005/0137454 A1* | 6/2005 | Saadat | ............ | A61B 1/0008 600/114 |
| 2005/0137455 A1* | 6/2005 | Ewers | ............ | A61B 1/0055 600/114 |
| 2005/0137456 A1* | 6/2005 | Saadat | ............ | A61B 1/31 600/114 |
| 2005/0137457 A1* | 6/2005 | Machida | ............ | A61M 25/0662 600/115 |
| 2005/0159644 A1* | 7/2005 | Takano | ............ | A61B 1/01 600/115 |
| 2005/0165273 A1* | 7/2005 | Takano | ............ | A61B 1/00082 600/116 |
| 2005/0171400 A1* | 8/2005 | Itoi | ............ | A61B 1/00006 600/114 |
| 2005/0215855 A1* | 9/2005 | Machida | ............ | A61B 1/273 600/114 |
| 2005/0215856 A1* | 9/2005 | Fujikura | ............ | A61B 1/00156 600/116 |
| 2005/0222496 A1* | 10/2005 | Sekiguchi | ........ | A61B 1/00082 600/115 |
| 2005/0222500 A1* | 10/2005 | Itoi | ............ | A61B 1/0005 600/180 |
| 2006/0025652 A1* | 2/2006 | Vargas | ............ | A61B 1/00154 600/114 |
| 2006/0100480 A1* | 5/2006 | Ewers | ............ | A61B 1/00082 600/114 |
| 2006/0111610 A1* | 5/2006 | Machida | ............ | A61B 1/00091 600/116 |
| 2006/0116549 A1* | 6/2006 | Sekiguchi | ........ | A61B 1/00055 600/116 |
| 2006/0135847 A1* | 6/2006 | Koch | ............ | A61B 1/0058 600/104 |
| 2006/0135848 A1* | 6/2006 | Koch | ............ | A61B 1/0058 600/104 |
| 2006/0271095 A1* | 11/2006 | Rauker | ............ | A61B 1/00082 606/197 |
| 2006/0287666 A1* | 12/2006 | Saadat | ............ | A61M 25/1011 606/198 |
| 2007/0010785 A1* | 1/2007 | Sekiguchi | ........ | A61B 1/00082 604/95.03 |
| 2007/0015965 A1* | 1/2007 | Cox | ............ | A61B 1/0052 600/114 |
| 2007/0043261 A1* | 2/2007 | Watanabe | ........ | A61B 1/00078 600/144 |
| 2007/0249901 A1* | 10/2007 | Ohline | ............ | A61B 5/068 600/117 |
| 2007/0270645 A1* | 11/2007 | Ikeda | ............ | A61B 1/015 600/116 |
| 2007/0299308 A1* | 12/2007 | Fujikura | ............ | A61B 17/3417 600/115 |
| 2008/0033246 A1* | 2/2008 | Matsui | ............ | A61B 1/00154 600/115 |
| 2008/0146875 A1* | 6/2008 | Noguchi | ............ | A61B 1/31 600/117 |
| 2008/0228034 A1* | 9/2008 | Fujikura | ............ | A61B 1/00082 600/114 |
| 2008/0249356 A1* | 10/2008 | Motai | ............ | A61B 1/00082 600/114 |
| 2009/0062608 A1* | 3/2009 | Miyoshi | ............ | A61B 1/00082 600/115 |
| 2009/0118582 A1* | 5/2009 | Tsumaru | ............ | A61B 1/00094 600/114 |
| 2009/0124857 A1* | 5/2009 | Viola | ............ | A61B 1/0055 600/141 |
| 2009/0124978 A1* | 5/2009 | Abrams | ............ | A61M 25/0662 604/164.01 |

(56) References Cited

U.S. PATENT DOCUMENTS

| | | | | |
|---|---|---|---|---|
| 2009/0156896 | A1* | 6/2009 | Kura | A61B 1/00039 600/118 |
| 2009/0287051 | A1* | 11/2009 | Itoi | A61B 1/0005 600/115 |
| 2010/0022832 | A1* | 1/2010 | Makiyama | A61B 1/01 600/115 |
| 2010/0286479 | A1* | 11/2010 | Ashida | A61B 1/018 600/116 |
| 2010/0292537 | A1* | 11/2010 | Ashida | A61B 1/00082 600/116 |
| 2011/0004063 | A1* | 1/2011 | Nakamura | A61B 1/31 600/115 |
| 2011/0137120 | A1* | 6/2011 | Itoi | A61B 1/12 600/114 |
| 2011/0137121 | A1* | 6/2011 | Itoi | A61B 1/12 600/114 |
| 2012/0071722 | A1 | 3/2012 | Nakamura et al. | |
| 2012/0220829 | A1* | 8/2012 | Fujikura | A61B 1/015 600/115 |
| 2012/0232347 | A1* | 9/2012 | Fujikura | A61B 17/3415 600/115 |
| 2013/0023920 | A1* | 1/2013 | Terliuc | A61B 1/00057 606/192 |
| 2014/0018625 | A1* | 1/2014 | Lal | A61B 1/31 600/115 |
| 2014/0094649 | A1* | 4/2014 | Ito | A61B 5/6885 600/103 |

FOREIGN PATENT DOCUMENTS

| | | |
|---|---|---|
| JP | H10-192223 | 7/1998 |
| JP | H10-248794 | 9/1998 |
| JP | 2000-237124 | 9/2000 |
| JP | 2003-260021 | 9/2003 |
| JP | 2005-334474 | 12/2005 |
| JP | 2006218231 | 8/2006 |
| JP | 2012-065798 | 4/2012 |
| JP | 2013-027466 | 2/2013 |
| JP | 2013-090875 | 5/2013 |
| JP | 2014083293 | 5/2014 |
| WO | 2011016428 | 2/2011 |

OTHER PUBLICATIONS

"Office Action of Japan Counterpart Application", dated Feb. 2, 2018, with English translation thereof, p. 1-p. 8.

"Office Action of Japan Counterpart Application," dated Jun. 11, 2018, with English translation thereof, p. 1-p. 6.

"Office Action of Japan Counterpart Application," with English translation thereof, dated Jul. 19, 2019, p. 1-p. 6.

"Office Action of China Counterpart Application," dated Mar. 14, 2019, with English translation thereof, p. 1-p. 13.

Office Action of China Counterpart Application, with English translation thereof, dated Jul. 11, 2019, pp. 1-13.

"Office Action of Japan Counterpart Application," with English translation thereof, dated Nov. 29, 2019, p. 1-p. 4.

"Office Action of China Counterpart Application", dated Jan. 10, 2020, with English translation thereof, pp. 1-15.

"Office Action of China Counterpart Application" with English translation thereof, dated Jun. 28, 2021, p. 1-p. 13.

"Reexamination Decision of China Counterpart Application" with English translation thereof, dated Oct. 8, 2021, p. 1-p. 26.

* cited by examiner

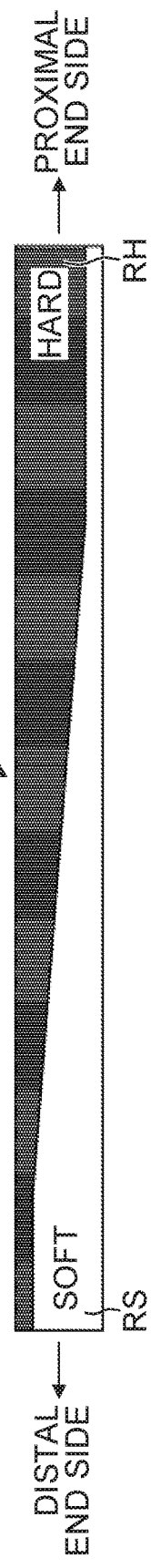
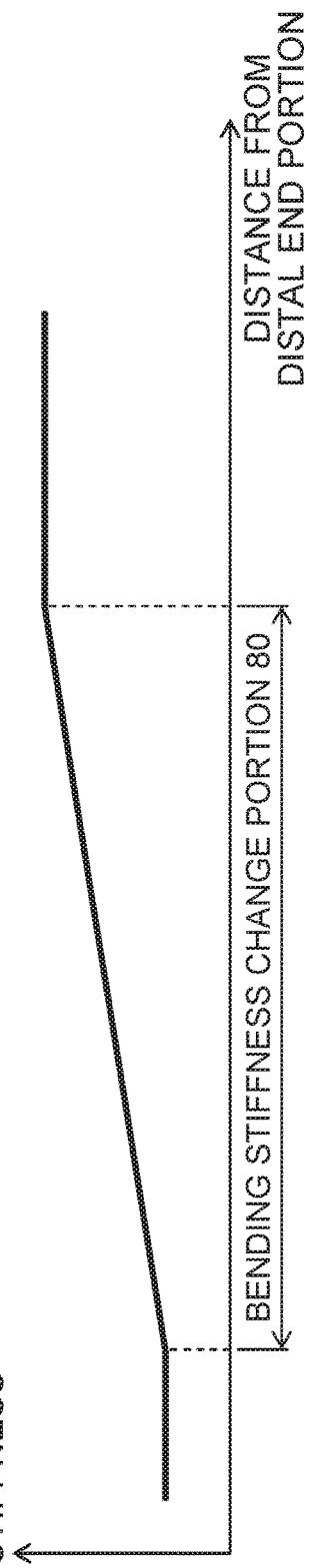
FIG.4A
FIG.4B
FIG.4C

ENDOSCOPE SYSTEM

CROSS-REFERENCE TO RELATED APPLICATIONS

The patent application claims priority under 35 U.S.C. § 119 to Japanese Patent Application No. 2015-021096, filed on Feb. 5, 2015. Each of the above application(s) is hereby expressly incorporated by reference, in its entirety, into the present application.

BACKGROUND OF THE INVENTION

Field of the Invention

The present invention relates to an endoscope system which combines and uses an endoscope and an insertion assisting tool, and particularly relates to the bending stiffness of an insertion portion of an endoscope.

Description of the Related Art

An endoscope may be used in the diagnosis and operation of a stomach, a duodenum and a small intestine, and so on. Further, it is known that the hardness of an insertion portion of the endoscope is changed according to the operator's operation in order to improve the insertion performance of the endoscope at diagnosis and operation (for example, see Japanese Patent Application Laid-Open No. 2013-027466 and Japanese Patent Application Laid-Open No. 2003-260021).

However, if a conventional endoscope like Japanese Patent Application Laid-Open No. 2013-027466 and Japanese Patent Application Laid-Open No. 2003-260021 is used alone in diagnosis and operation, an insertion portion does not become a straight state due to adhesion by operation and the fixing of an intestinal tract by the ligament of Treitz, and so on, the insertion portion warps (deflects) inside a stomach, and so on, the insertion force is not transmitted to a distal end portion, and there are many cases where the distal end portion cannot move forward, which is a so-called "difficult insertion case". Therefore, there is suggested an endoscope system which combines and uses an endoscope with a balloon and an overtube (insertion assisting tool) with a balloon (for example, see Japanese Patent Application Laid-Open No. 2013-090875). Moreover, even in such an endoscope system, a technique that can change a hardness of an insertion portion of an endoscope is known (for example, see Japanese Patent Application Laid-Open No. 2005-334474).

SUMMARY OF THE INVENTION

In a conventional endoscope system as described in Japanese Patent Application Laid-Open No. 2013-090875 and Japanese Patent Application Laid-Open No. 2005-334474, when an insertion portion of an endoscope is inserted into an overtube, the insertion portion is slidden at a predetermined stroke (decided by the relationship between the effective length of the insertion portion of the endoscope and the length of the overtube) with respect to the overtube. In such a slide state, since the distal end side of the insertion portion is exposed from the overtube and the insertion portion is not covered with the overtube, the insertion portion has the bending stiffness attributable to the insertion portion itself and becomes easy to bend. Meanwhile, if the whole length of the overtube is made relatively long relative to the insertion portion in order to secure bending stiffness, since slidable length becomes short and insertion itself becomes difficult, it is not possible to make the overtube too long.

Moreover, in a postoperative patient of the Roux-en-Y Method or the like, the degree of bending stiffness required for the insertion portion and the position and range in which the bending stiffness is required vary depending on conditions such as the removal range of a stomach (total removal or half removal) and an observation position, but, in the prior art as described in above-mentioned Japanese Patent Application Laid-Open No. 2013-027466, Japanese Patent Application Laid-Open No. 2003-260021, Japanese Patent Application Laid-Open No. 2013-090875, and Japanese Patent Application Laid-Open No. 2005-334474, it is difficult to respond to a request of bending stiffness that varies for each such patient.

The present invention is made considering such circumferences, and aims to provide an endoscope system which can secure appropriate bending stiffness of an insertion portion while maintaining the slide length of the insertion portion.

To achieve the above-mentioned object, an endoscope system according to a first aspect of the present invention includes: an endoscope configured to include an insertion portion to be inserted into a body and an operation portion connected with a proximal end side of the insertion portion, where the insertion portion includes a distal-end hard portion, a bending portion connected with a proximal end side of the distal-end hard portion and a flexible portion connected with a proximal end side of the bending portion; and an insertion assisting tool configured to include a tube body with a distal end opening and a proximal end opening, the tube body including an insertion path into which the insertion portion is inserted from the proximal end opening, where the insertion portion is movable forward and backward in a longitudinal axis direction of the tube body and the tube body is formed to have a length in which at least a part of the flexible portion projects from the distal end opening when the insertion portion is located in a distal end position in a movable range with respect to the tube body, wherein: the flexible portion includes a projection region which projects from the distal end opening when the insertion portion is located in the distal end position in the movable range with respect to the tube body; and the projection region includes a bending stiffness change portion in which a bending stiffness increases from a first position on a distal end side toward a second position on a proximal end side.

According to the first aspect of the present invention, since the projection region in which the flexible portion of the endoscope projects from the distal end opening of the insertion assisting tool includes the bending stiffness change portion in which the bending stiffness increases from the distal end side to the proximal end side, it is possible to secure necessary bending stiffness even in the projection region in which the flexible portion projects from the distal end of the insertion assisting tool. Therefore, it is not necessary to lengthen the insertion assisting tool, and it is possible to maintain the slide length of the insertion portion. Moreover, since the flexible portion includes such the bending stiffness change portion, it is possible to secure necessary bending stiffness by adequately setting the stiffness of the bending stiffness change portion, and the flexible portion can be designed so as not to needlessly warp in the projection region. In addition, by adequately setting a range in which the bending stiffness change portion is provided and the stiffness in the bending stiffness change portion, it is possible to secure appropriate bending stiffness of the insertion portion in response to a required bending stiffness that varies for each patient while maintaining the slide length of the insertion portion.

Here, a change in the bending stiffness in the bending stiffness change portion may be designed such that the bending stiffness uniformly increases from the first position toward the second position (the increasing rate of the bending stiffness is constant) or the increasing rate of the bending stiffness may be changed in the middle of the first position and the second position.

To achieve the above-mentioned object, an endoscope system according to a second aspect of the present invention includes: an endoscope configured to include an insertion portion to be inserted into a body and an operation portion connected with a proximal end side of the insertion portion, where the insertion portion includes a distal-end hard portion, a bending portion connected with a proximal end side of the distal-end hard portion and a flexible portion connected with a proximal end side of the bending portion; and an insertion assisting tool configured to include a tube body with a distal end opening and a proximal end opening, the tube body including an insertion path into which the insertion portion is inserted from the proximal end opening, where the insertion portion is movable forward and backward in a longitudinal axis direction of the tube body, wherein: the insertion assisting tool includes an abutting portion which abuts on the endoscope on a proximal end side of the tube body, and the tube body is formed to have a length in which at least a part of the flexible portion projects from the distal end opening when the endoscope abuts on the abutting portion; the flexible portion includes a projection region which projects from the distal end opening when the endoscope abuts on the abutting portion; and the projection region includes a bending stiffness change portion in which a bending stiffness increases from a first position on a distal end side toward a second position on a proximal end side.

According to the second aspect of the present invention, in a similar way to the first aspect, it is possible to secure appropriate bending stiffness of the insertion portion while maintaining the slide length of the insertion portion. Here, even in the second aspect, a change in the bending stiffness in the bending stiffness change portion may be designed such that the bending stiffness uniformly increases from the first position toward the second position (the increasing rate of the bending stiffness is constant) or the increasing rate of the bending stiffness may be changed in the middle of the first position and the second position.

As for an endoscope system according to a third aspect, in the first or second aspect, the first position is a distal end position of the projection region and the second position is a proximal end position of the projection region. The third aspect defines the distal end position and proximal end position of the bending stiffness change portion.

As for an endoscope system according to a fourth aspect, in the first or second aspect, the projection region includes a bending stiffness uniform portion on a distal end side from the first position, and the bending stiffness uniform portion has constant bending stiffness along a longitudinal axis direction of the flexible portion. According to the fourth aspect, by providing a bending stiffness uniform portion with uniform bending stiffness on the distal end side than the first position in the projection region, even if the endoscope is pressed in a state where a bending portion bent at the time of insertion contacts with a wall surface inside a body, this bending stiffness uniform portion bends and absorbs the pressing force, and it is possible to mitigate a load into the body.

As for an endoscope system according to a fifth aspect, in any one of the first to fourth aspects, the second position is a proximal end position of the projection region; and the bending stiffness change portion is formed from the first position to the second position and is further formed up to a third position on a proximal end side than the projection region in the flexible portion That is, in the fifth aspect, the bending stiffness change portion is also provided in a portion (non-projection region) which does not project from the distal end opening when the insertion portion is located in the distal end position in the movable range with respect to the tube body. According to the fifth aspect, in a portion in which the bending stiffness changes, a change in the curvature radius at the time of bending operation can be absorbed in the insertion assisting tool (non-projection region).

As for an endoscope system according to a sixth aspect, in the first or second aspect, the second position is located on a distal end side than a proximal end position of the projection region. That is, in the sixth aspect, the bending stiffness change portion is provided in a part of the projection region instead of the whole of the projection region. By this means, it is possible to prevent a warpage (deflection) of the insertion portion in a body and make the distal-end hard portion move forward easily.

As for an endoscope system according to a seventh aspect, in any one of the first to sixth aspects, a maximum bending stiffness of the bending stiffness change portion is twice or more as large as a minimum bending stiffness. When the endoscope is inserted, depending on a site to be inserted, the distal-end hard portion becomes difficult to move forward by a small flexure and the flexible portion becomes easy to warp (deflects) before the distal-end hard portion, but, according to the seventh aspect, it is possible to prevent warpage (deflection) even in a state where the flexible portion is likely to warp, and it is possible to facilitate the insertion of the endoscope.

As for an endoscope system according to an eighth aspect, in any one of the first to seventh aspects a difference between a maximum bending stiffness and a minimum bending stiffness of the bending stiffness change portion is greater than a half of a bending stiffness of a maximum bending stiffness portion in the tube body. The eighth aspect increases an effect of providing the bending stiffness change portion by making the difference between the maximum bending stiffness and the minimum bending stiffness in the bending stiffness change portion greater than the half of the bending stiffness of the tube body.

As described above, according to an endoscope system of the present invention, it is possible to secure appropriate bending stiffness of an insertion portion while maintaining the slide length of the insertion portion.

Figure 5:
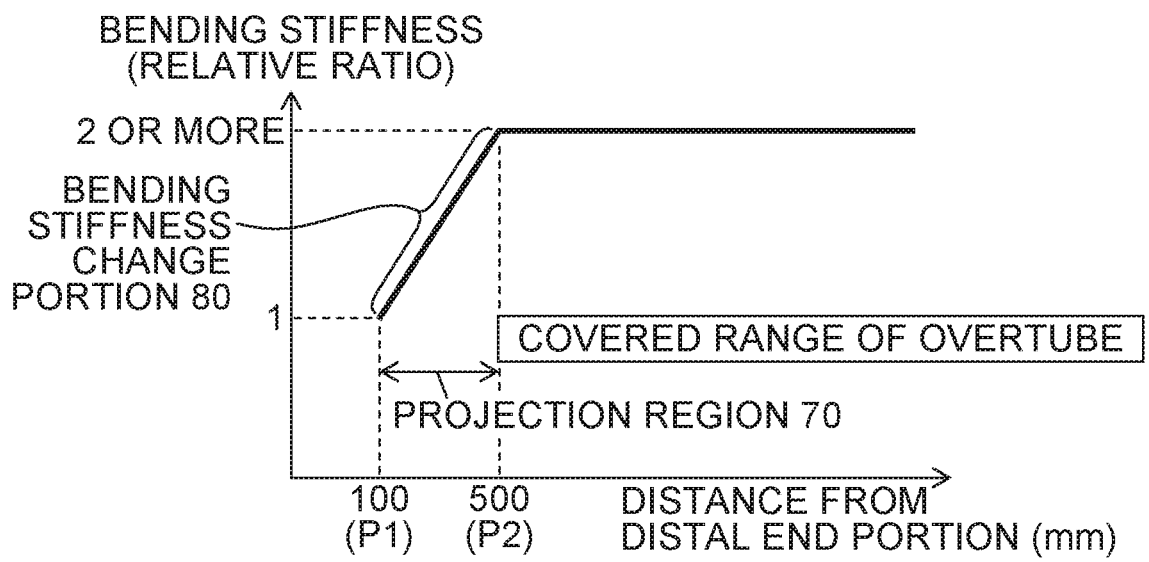
Figure 6:
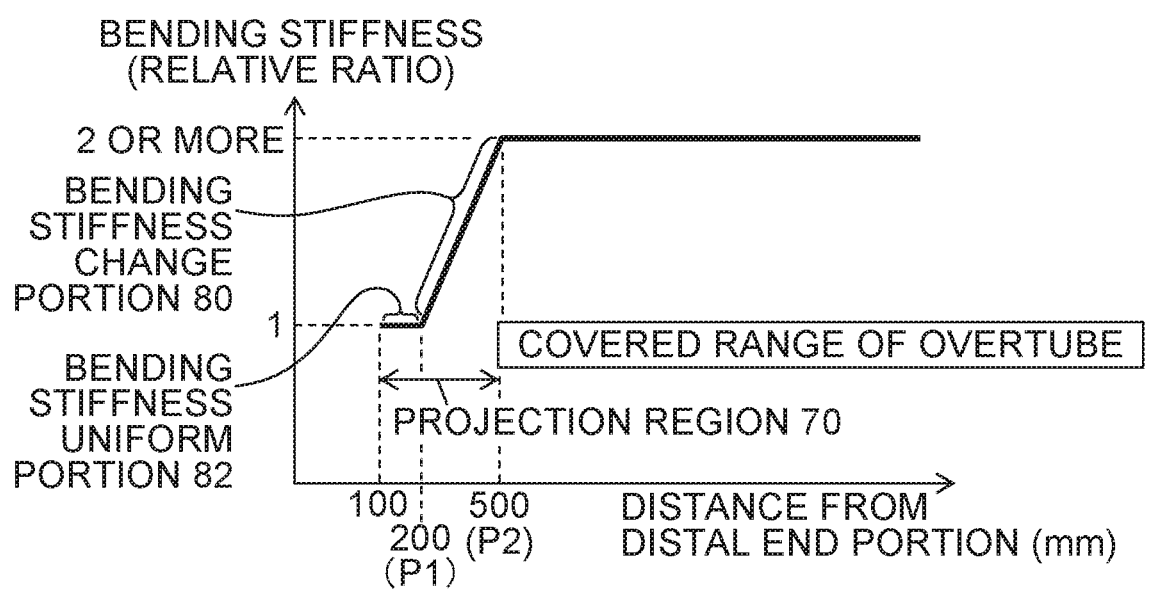
Figure 7A:
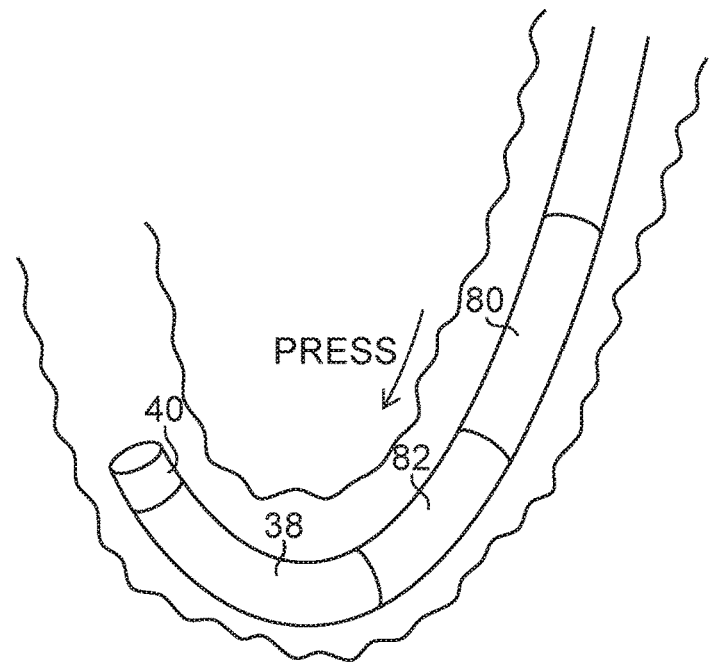
Figure 7B:
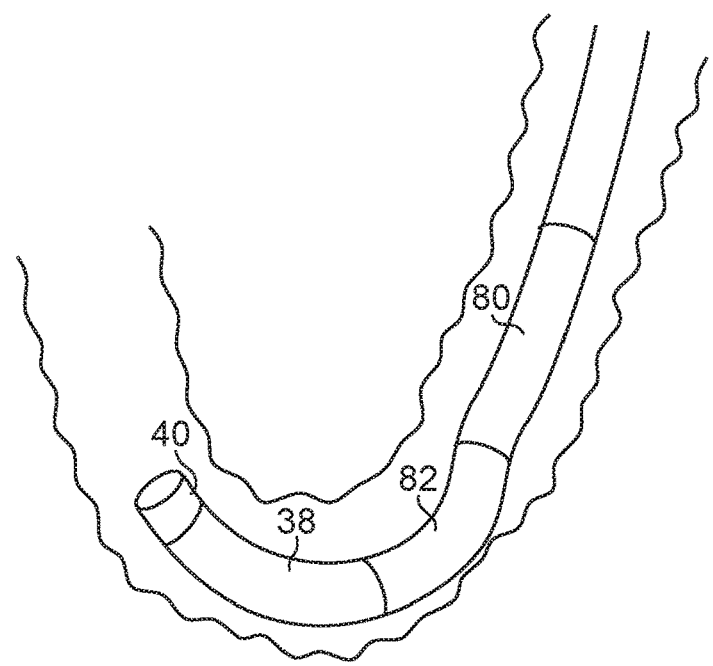
Figure 8:
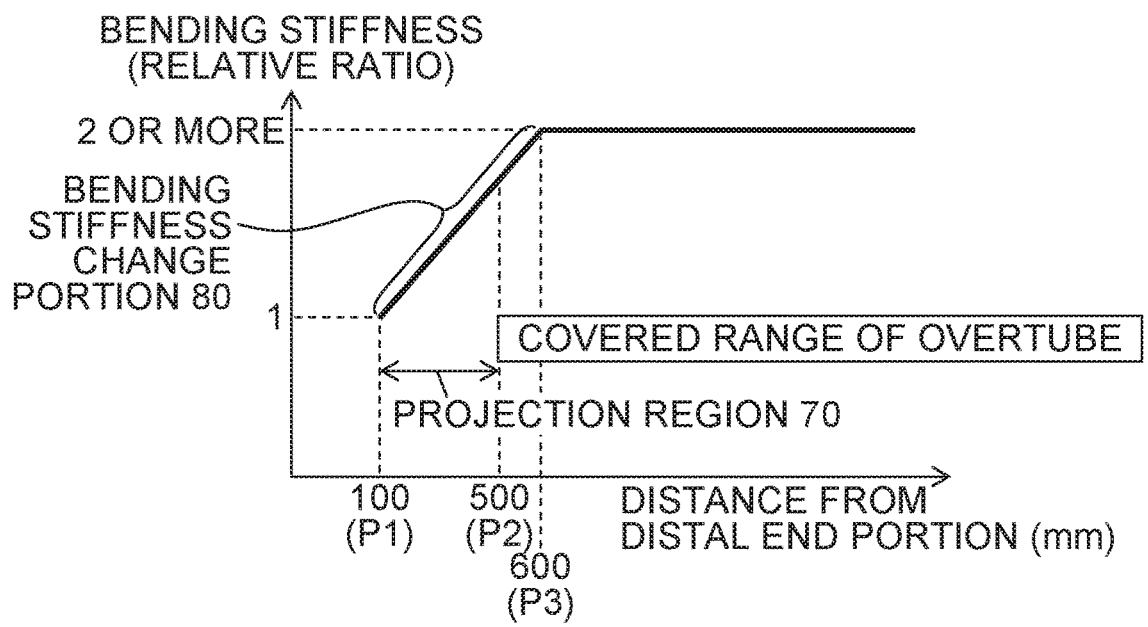
Figure 9:
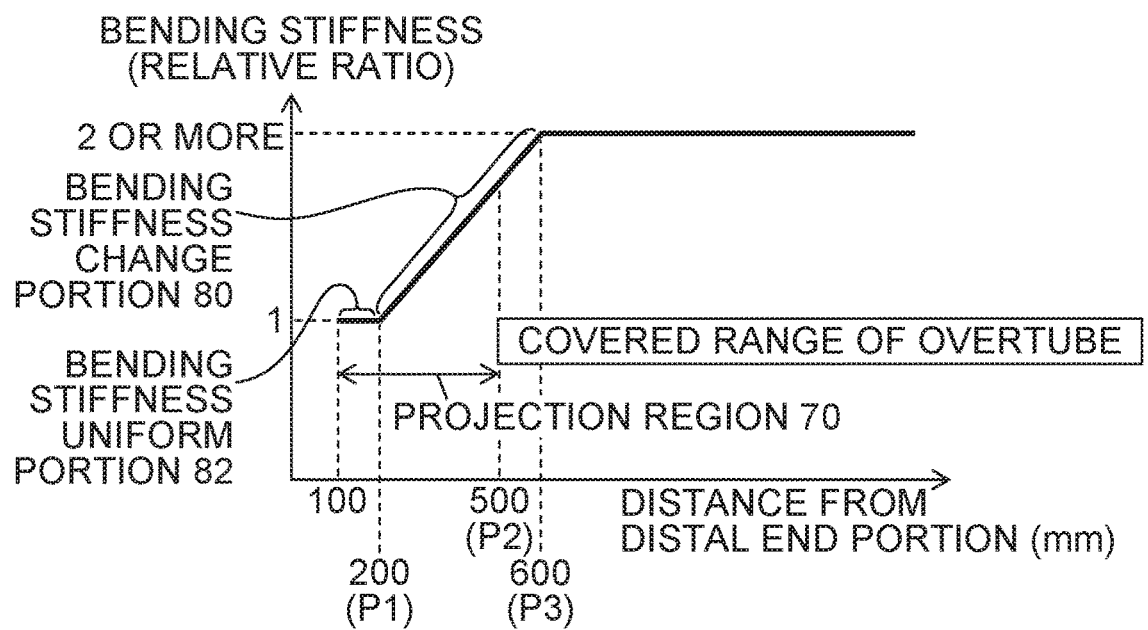
Figure 10:
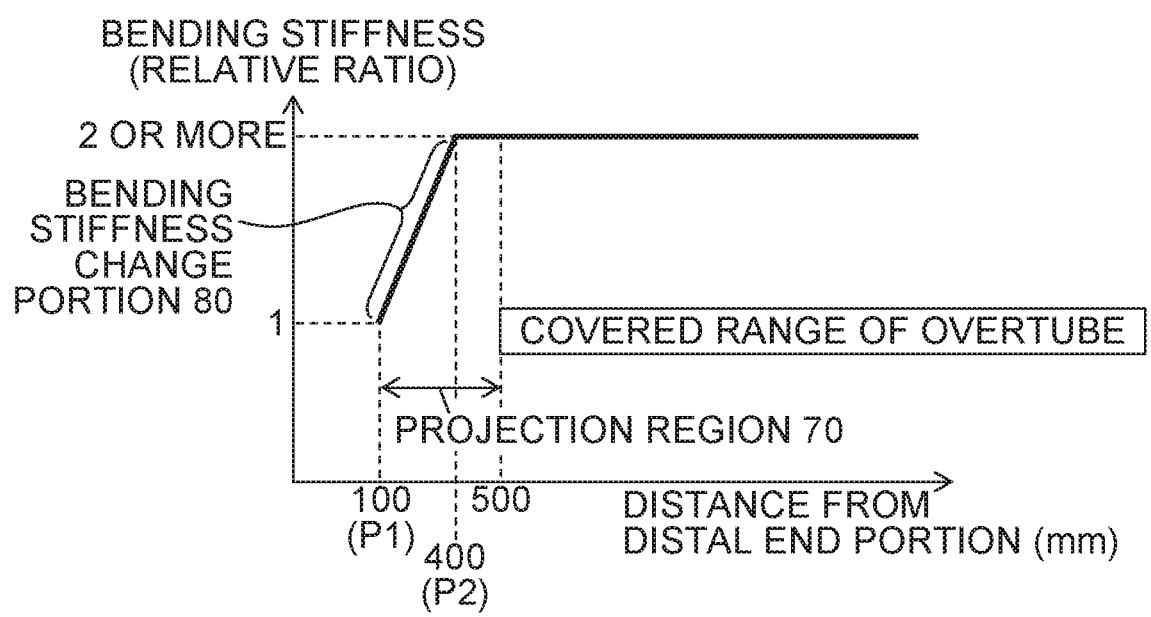
Figure 11:
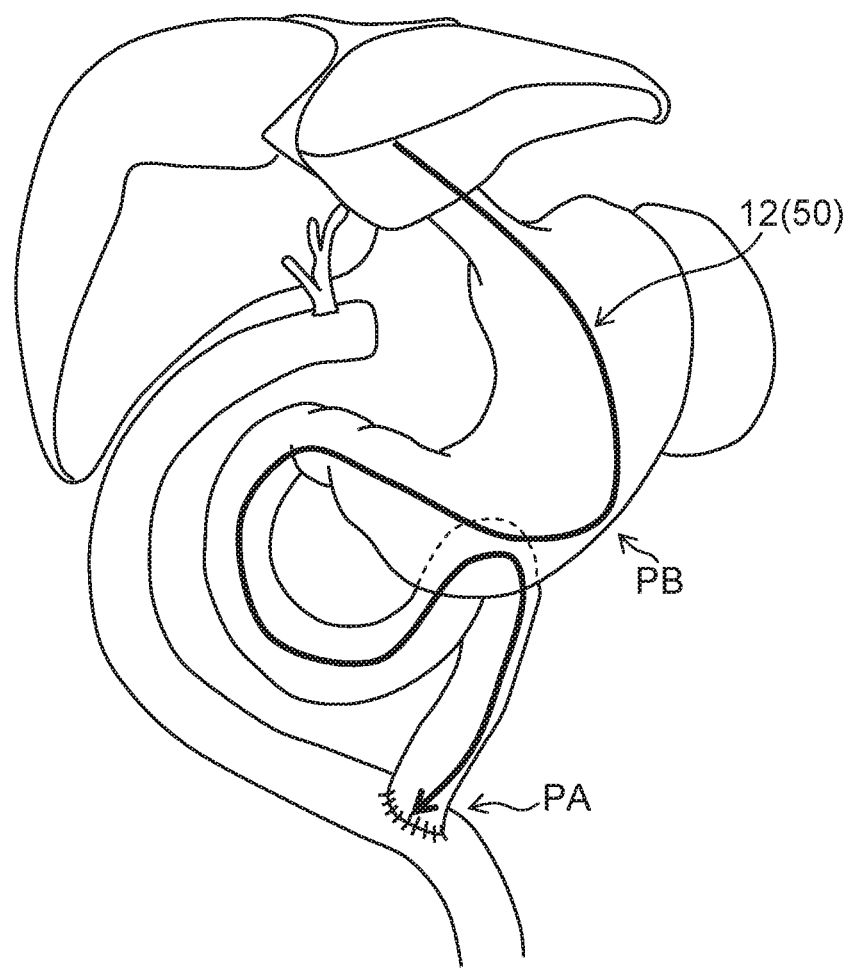
Figure 12A:
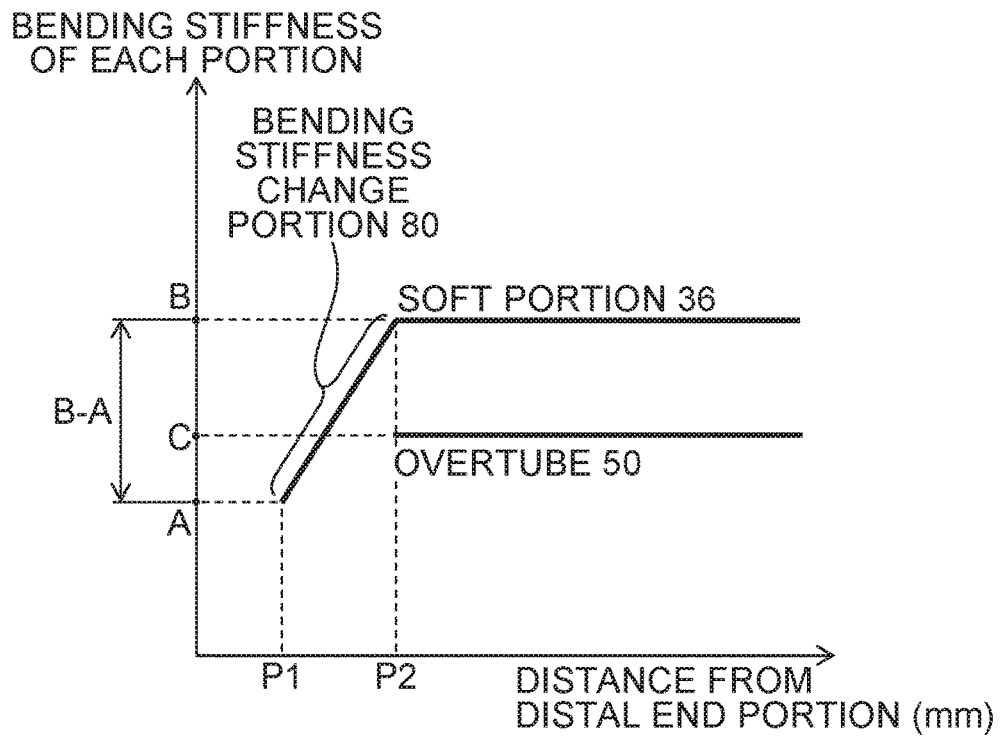
Figure 12B:
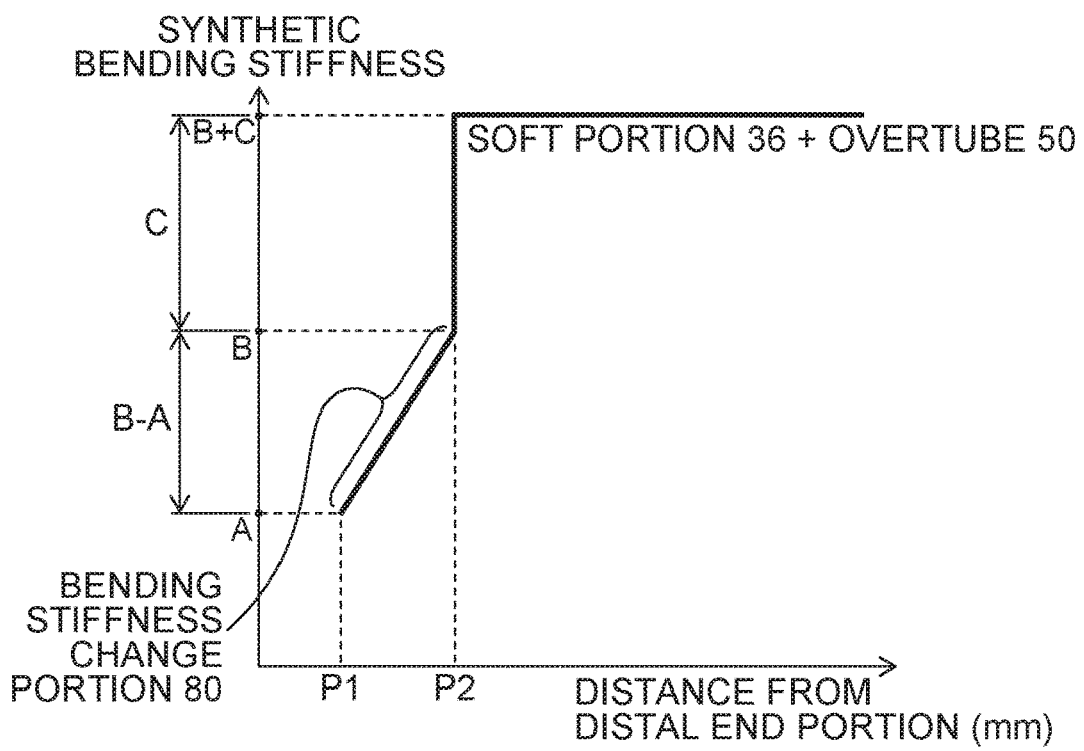
Figure 13:
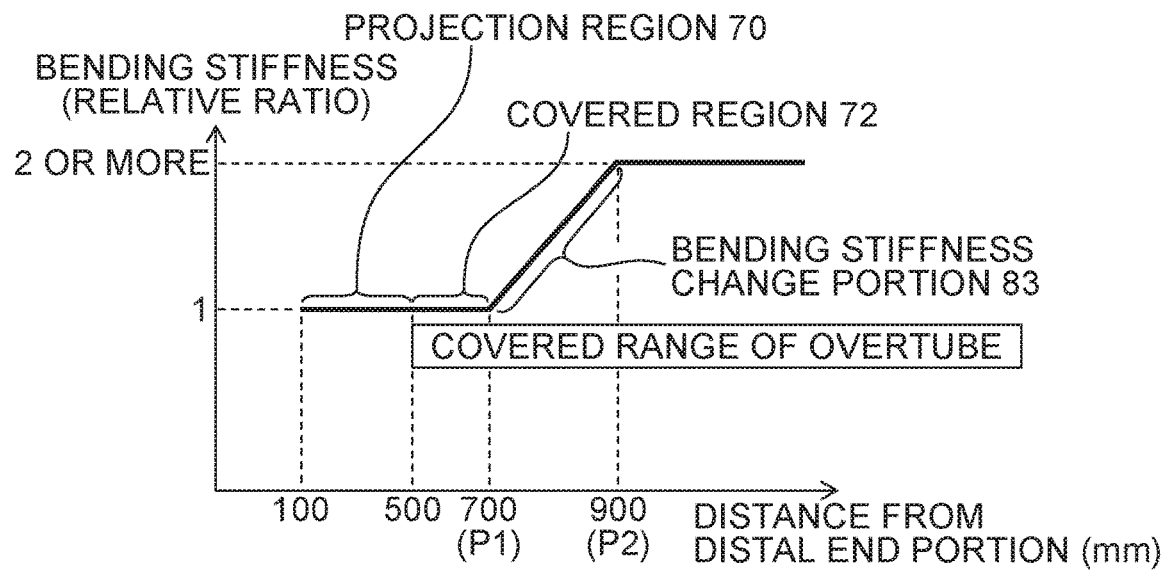
Figure 14:
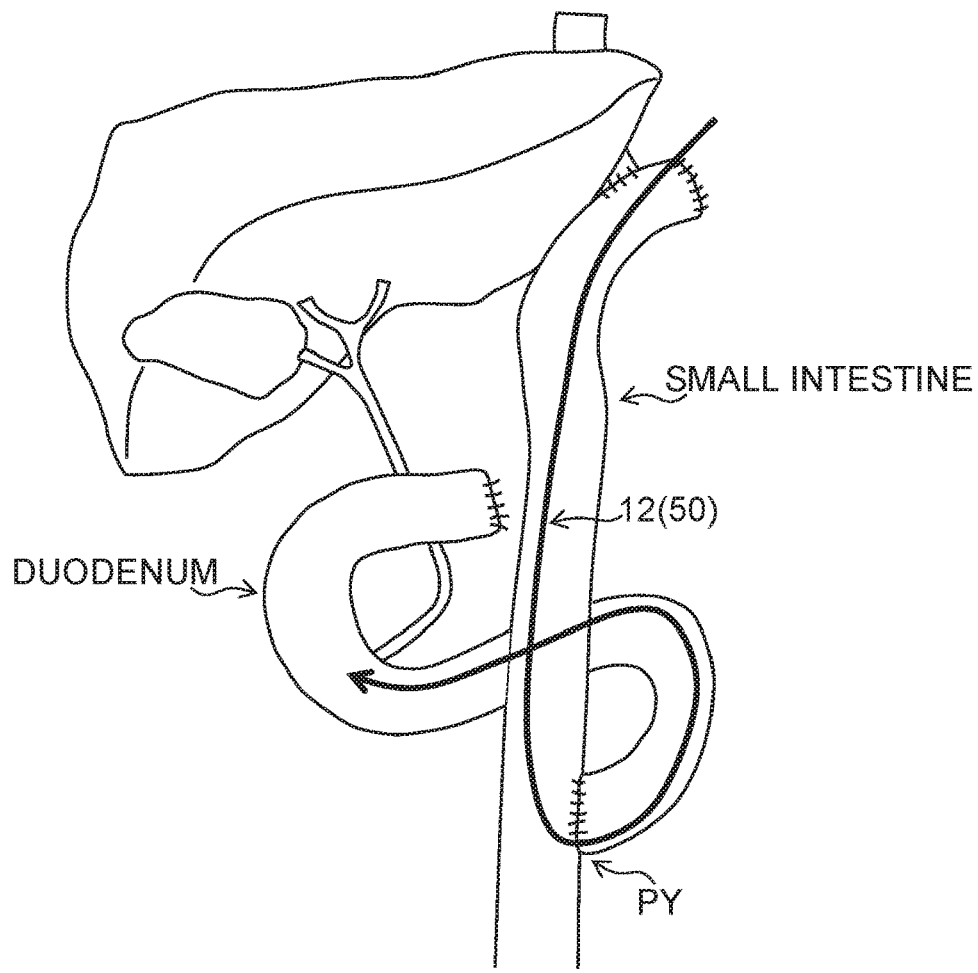

illustrates a state where the insertion portion 12 is maximally projected in a movable range;

FIGS. 4A to 4C are diagrams illustrating examples of changing bending stiffness depending on the material configuration of a shell 37E of the insertion portion 12;

FIG. 5 is a graph illustrating bending stiffness in the first example;

FIG. 6 is a graph illustrating bending stiffness in the second example;

FIGS. 7A and 7B are diagrams illustrating the appearance of insertion into a body in the second example;

FIG. 8 is a graph illustrating bending stiffness in the third example;

FIG. 9 is a graph illustrating bending stiffness in a case where a bending stiffness uniform portion 82 is provided in the distal end portion of a projection region 70 in the third example;

FIG. 10 is a graph illustrating bending stiffness in the fourth example;

FIG. 11 is a diagram illustrating the appearance of insertion into a body in the fourth example;

FIGS. 12A and 12B are graphs illustrating the stiffness of the flexible portion 36 and the overtube 50;

FIG. 13 is a graph illustrating bending stiffness in other inventions (another invention); and FIG. 14 is a diagram illustrating the appearance in which an insertion portion of an endoscope system in other inventions (another invention) is inserted into the body of a subject.

DETAILED DESCRIPTION OF THE PREFERRED EMBODIMENTS

Figure 1:
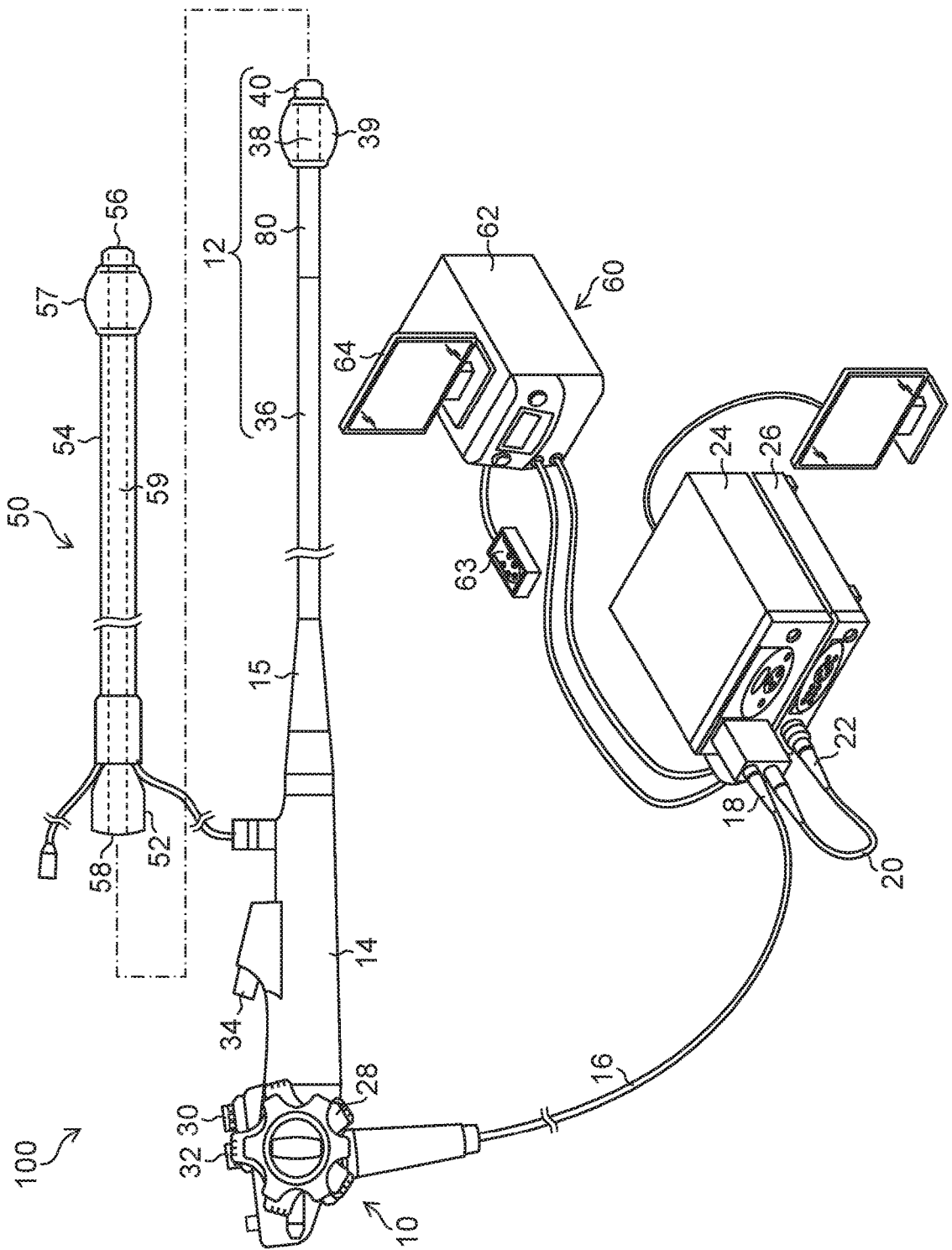
FIG. 1 is a diagram illustrating the configuration of an endoscope system according to one embodiment of the present invention.

In the following, an endoscope system according to the present invention is described with reference to the accompanying drawings. FIG. 1 is a diagram illustrating the whole configuration of an endoscope system 100 according to the present embodiment.

<Whole Configuration of Endoscope System>

As illustrated in FIG. 1, an endoscope system 100 includes an endoscope 10 and an overtube 50. The endoscope 10 includes an insertion portion 12 to be inserted into a body of a subject, and a hand operation portion 14 is coupled with a proximal end portion of the insertion portion 12. A universal cord 16 is connected with the hand operation portion 14, and a light source connector 18 is provided in a distal end of the universal cord 16. Moreover, a cable 20 diverges from the light source connector 18, and a processor connector 22 is provided in a distal end of the cable 20. The light source connector 18 and the processor connector 22 are respectively connected with a light source device 24 and a processor device 26 in a detachable manner. Here, the overtube 50 is one aspect of an insertion assisting tool.

<Configuration of Overtube>

The overtube 50 includes a holding portion 52 to be held by an operator, and a tube body 54. The holding portion 52 is in a cylindrical object formed with a hard material such as resin. The tube body 54 is formed in a cylindrical shape having a distal end opening 56 and a proximal end opening 58 by a flexible material such as polyurethane, an inside of this cylindrical portion is an insertion path 59 in which the insertion portion 12 is inserted, and the insertion portion 12 can freely move forward and backward in a longitudinal axis direction of the overtube 50 (an X direction in FIG. 3). Moreover, as described later, in a state where the insertion portion 12 is located in the distal end position in a movable range with respect to the overtube 50, an inner edge of the proximal end opening 58 abuts on a boot 15 of the insertion portion 12. That is, the inner edge of the proximal end opening 58 forms an abutting portion in this aspect.

Moreover, a balloon 57 is attached to an outer peripheral surface at the distal end portion of the tube body 54. The balloon 57 is formed in a cylindrical shape with an elastic member such as rubber, and has an expansion portion at the center. The balloon 57 is attached and fixed to the outer peripheral surface at the distal end portion of the tube body 54, and is expanded or contracted by fluid (such as air and water) supplied/sucked through an unillustrated fluid conduit. Such expansion/contraction control of the balloon 57 is performed by a balloon controlling device 60. The balloon controlling device 60 is a device that supplies/sucks fluid or performs pressure control in order to expand/contract the balloon 57 or maintain the state, and includes a device body 62 in which a pump and a sequencer, and so on, are provided, a hand switch 63 and a balloon monitor 64.

<Whole Configuration of Insertion Portion>

The insertion portion 12 is formed by coupling a flexible portion 36, a bending portion 38 and a distal-end hard portion 40 in this order from the proximal end side (the side of the hand operation portion 14) to the distal end side. The boot 15 of the insertion portion 12 is provided in the most proximal end side of the flexible portion 36. The boot 15 has a function to prevent the proximal end portion of the flexible portion from being folded. The boot 15 is processed so as to have a diameter which gradually becomes thin from the proximal end side to the distal end side (taper processing).

<Configuration of Hand Operation Portion>

The hand operation portion 14 is provided with an angle knob 28 for a bending operation, an air-supply and water-supply button 30 to jet air and water, and so on, from the distal end of the insertion portion 12 (an opening provided in the distal-end hard portion 40 described later), and a suction button 32, and so on. Moreover, a forceps entrance 34 in which various treatment tools are inserted is provided on the side of the insertion portion 12 of the hand operation portion 14.

Moreover, air and water are supplied from an air-supply and water-supply device incorporated in the light source device 24 according to the operation of the air-supply and water-supply button 30, and are jetted from the above-mentioned air-supply and water-supply nozzle to an observation window. A forceps exit is connected with an unillustrated forceps channel provided in the insertion portion 12, and is communicated with the forceps entrance 34. The distal end of a treatment tool inserted into the forceps entrance 34 is exposed from the forceps exit.

<Configuration of Flexible Portion>

Figure 2:
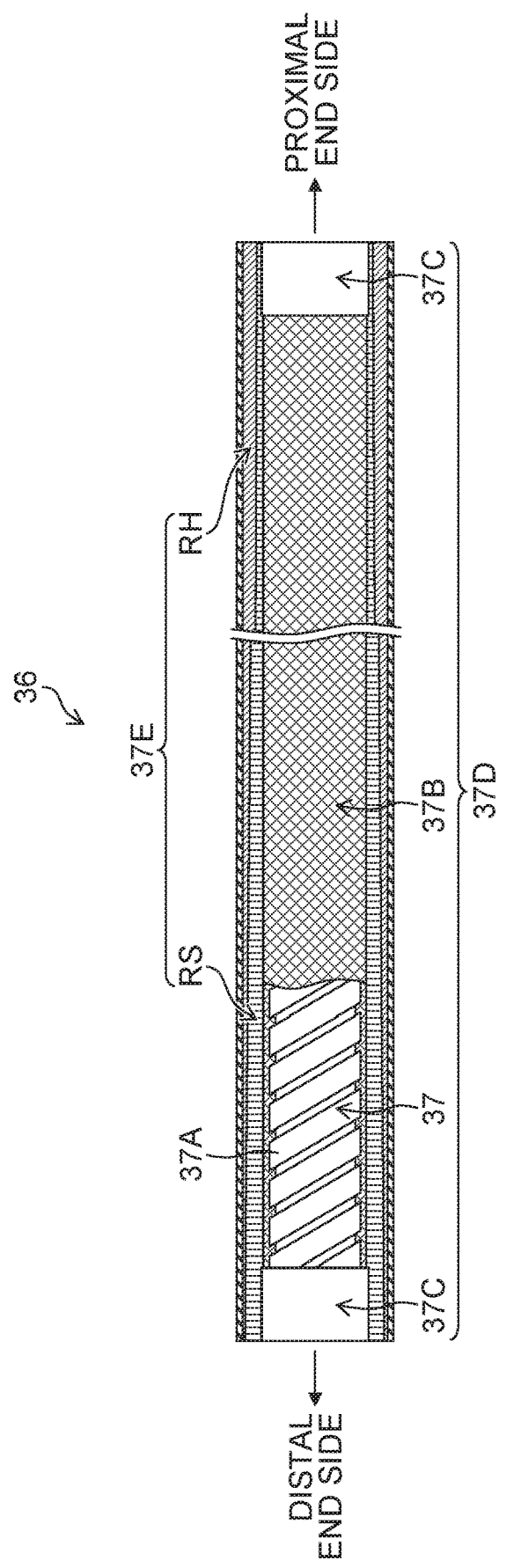
FIG. 2 is a cross-sectional drawing illustrating the structure of a flexible portion 36 (near a bending stiffness change portion)

As illustrated in FIG. 2, the flexible portion 36 has a configuration in which: a spiral tube 37 formed by winding a thin elastic belt-shaped plate 37A in a spiral manner is provided in the innermost side; the outside of the spiral tube 37 is covered with a net body 37B made of metal wire and caps 37C are fitted to both ends thereof to form a tubular body 37D; and a shell 37E formed with resin is layered in the outer peripheral surface of the tubular body 37D. Moreover, as described later, a bending stiffness change portion 80 (see FIG. 1) in which bending stiffness changes along the longitudinal axis direction (the X direction in FIG. 3) is provided in a part of the flexible portion 36.

<Configuration of Bending Portion>

The bending portion 38 has a configuration in which: a structure is formed by coupling unillustrated angle rings in a mutually rotatable manner; and a net-like body made of metal wire is covered on the outer periphery of this structure and is further covered with a shell made of rubber. A plurality of unillustrated operation wires extend from the hand operation portion 14 to the bending portion 38, and the distal end portions of these operation wires are fixed to an angle ring of a distal end portion forming the bending portion 38. By this means, the bending portion 38 is bent in the upper, lower, right or left direction according to the operation of the angle knob 28 provided in the hand operation portion 14. Moreover, a balloon 39 is attached to the outer periphery of the bending portion 38, and, in the same way as the above-mentioned balloon 57, is expanded or contracted by fluid (such as air and water) supplied/ejected through an unillustrated fluid conduit provided in the insertion portion 12.

<Configuration of Distal Hard Portion>

An optical system (such as a lens or imaging element, which is not illustrated) for taking an image in the subject is incorporated in the distal-end hard portion 40, and an observation window, an illumination window, an air-supply and water-supply nozzle, and a forceps exit, and so on, which are not illustrated, are provided in the distal end surface of the distal-end hard portion 40. The emission end of a light guide that guides a illumination light from the light source device 24 is provided in the back of the illumination window, and the illumination light guided by the light guide is emitted to an observation site in the subject through the above-mentioned illumination window.

<Projection Region>

Figure 3:
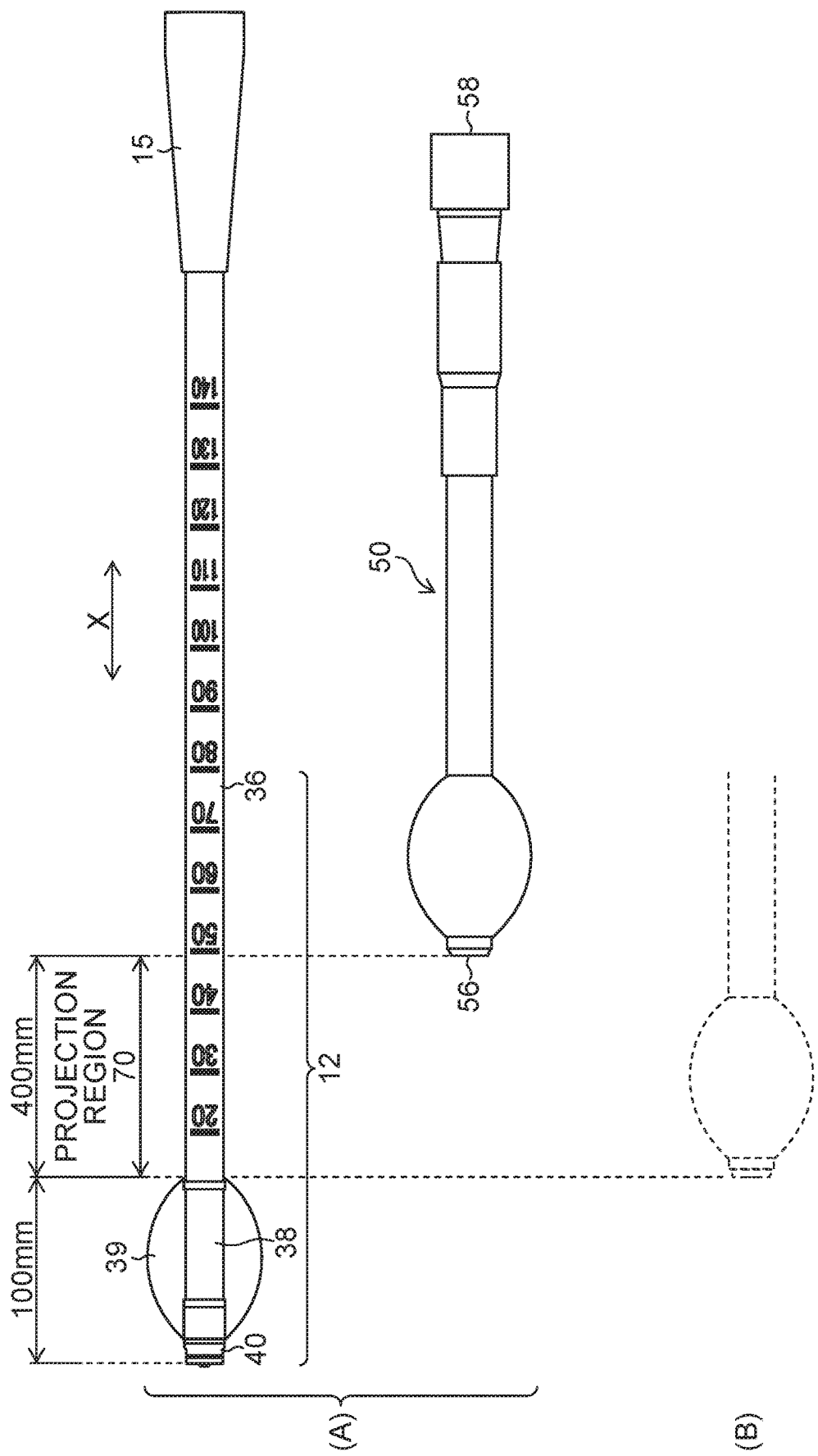
FIG. 3 is a diagram illustrating a slide range with respect to an overtube 50 of an insertion portion 12, in which Part (A) illustrates a state where a proximal end side of the insertion portion 12 abuts on the overtube 50 and Part (B)

Next, the projection region 70 (projection region) held by the flexible portion 36 is described. FIG. 3 is a diagram illustrating the positional relationship between the insertion portion 12 and the overtube 50. Here, in the present embodiment, a case where the effective length of the insertion portion 12 is 1520 mm and the total length of the overtube 50 is 1050 mm is described, but, in the present invention, the lengths of the insertion portion 12 and the overtube 50 are not limited to such a case. Moreover, FIG. 3 is provided to explain the relationship of respective elements, and does not accurately reflect an actual size and shape.

Part (A) in FIG. 3 is a diagram illustrating the positional relationship between the insertion portion 12 and the overtube 50 in a state where the insertion portion 12 is inserted into the overtube 50 and is slidden (moved) until the boot 15 provided on the proximal end side of the insertion portion 12 abuts on the overtube 50 (that is, until the insertion portion 12 is located in the distal end position in a movable range with respect to the overtube 50) (here, the insertion portion 12 and the overtube 50 are respectively illustrated in Part (A) and Part (B) in FIG. 3 to explain the positional relationship, but the insertion portion 12 is actually inserted into the overtube 50). In this positional relationship, the external diameter of the boot 15 is equal to the internal diameter of the proximal end opening 58 of the overtube 50, and, since the overtube 50 abuts on the boot 15, further slide to the distal end side of the overtube 50 of the insertion portion 12 is restricted.

In the state illustrated in Part (A) in FIG. 3, the distal-end hard portion 40, the bending portion 38 and a part of the flexible portion 36 in the insertion portions 12 are projected from the distal end opening 56 of the overtube 50. The length of these projection parts is 500 mm in the present embodiment, and a region in which the part of the flexible portion 36 projects in these is called "projection region 70 (projection region)" below. As described above, the balloon 39 is attached to the bending portion 38, and, since the bending portion 38 cannot be slidden in the overtube 50 (this state is shown by dotted lines in Part (B) in FIG. 3), the flexible portion 36 can slide in the overtube 50 within the range of the projection region 70 (that is, between the state illustrated in Part (A) in FIG. 3 and the state illustrated in Part (B) in FIG. 3).

Here, in the present embodiment, it is assumed that the total length of the distal-end hard portion 40 and the bending portion 38 is 100 mm. Therefore, the length of the projection region 70 is 400 mm.

<Bending Stiffness Change Portion>

In the present embodiment, the bending stiffness change portion 80 in which bending stiffness changes is provided in the projection region 70. As illustrated in FIG. 2, this bending stiffness change portion 80 can be realized by forming the shell 37E of the flexible portion 36 with resin layers RH and RS with different hardness and changing the thickness of those resin layers from the distal end side to the proximal end side. Specifically, as illustrated in FIG. 4A, the outside portion of the shell 37E is formed with a hard resin layer RH (bending stiffness is high), the inside portion is formed with a soft resin layer RS (bending stiffness is lower than resin layer RH), the resin layer RS is thickened in a first position P1 (first position) on the distal end side in the range of the bending stiffness change portion 80, and the resin layer RS is thinned and the resin layer RH is thickened from the first position P1 toward a second position P2 (second position) (it is assumed that the thickness total of resin layers RH and RS is constant). Thus, as illustrated in FIG. 4C, the bending stiffness in the bending stiffness change portion 80 can be uniformly increased from the distal end side toward the proximal end side (the increasing rate of the bending stiffness is constant).

Here, a change in the bending stiffness as illustrated in FIG. 4C can be realized even by changing the mixing ratio of the hard resin and the soft resin instead of changing the thickness of the resin layers. Specifically, as illustrated in FIG. 4B, it only has to raise the ratio of the soft resin (with low bending stiffness) on the distal end side and raise the ratio of the hard resin (with high bending stiffness) from the distal end side toward the proximal end side. Moreover, the bending stiffness may be increased by using a single resin instead of using a plurality of resins and by increasing the thickness of the resin layer (increasing the thickness of the shell 37E) from the distal end side toward the proximal end side.

Here, a case where the bending stiffness in the bending stiffness change portion 80 uniformly increases (the increasing rate of the bending stiffness is constant) from the distal end side toward the proximal end side has been described in the present embodiment, but the aspect of a change in the bending stiffness in the bending stiffness change portion is not limited to such a case in the present invention, and the bending stiffness increase rate may be changed from the distal end side toward the proximal end side.

<Insertion into Subject>

In the endoscope system 100 of the above-mentioned configuration, for example, the insertion portion 12 and the overtube 50 can be inserted into a subject as follows. Specifically, first, an operator holds the holding portion 52 and inserts the overtube 50 from the mouth of the subject into the body, controls the above-mentioned balloon controlling device 60 and expands the balloon 57 when a predetermined length is inserted, and fixes the overtube 50 to the subject. Further, the insertion portion 12 is inserted into the insertion path 59 of the overtube 50 in this state, and the insertion portion 12 is inserted into a deep portion of the subject until the boot 15 abuts on the inner periphery of the proximal end opening 58. In this state, since the insertion portion 12 is located in the distal end position in a movable range with respect to the overtube 50 and a part of the flexible portion 36 on the distal end side and the bending portion 38 are exposed from the distal end opening 56, the balloon controlling device 60 is controlled to expand the balloon 39, and the insertion portion 12 is fixed to the subject. Further, next, the balloon 57 is contracted to release the fixation of the overtube 50 in the subject, and the overtube 50 is inserted into the subject more deeply (until the distal end opening 56 is located in the proximal end portion of the bending portion 38). Further, the overtube 50 is fixed to the subject by the expansion of the balloon 57, the fixation state of the insertion portion 12 is released by the contraction of the balloon 39, and the insertion portion 12 is inserted into the subject more deeply. By repeating such procedures, it is possible to insert the insertion portion 12 and the overtube 50 in a desired site of the subject.

EXAMPLES

Next, a position and range in which the bending stiffness change portion 80 is provided and the value of the bending stiffness in the bending stiffness change portion 80 are described in detail according to each example. Here, a case where the insertion portion 12 and the overtube 50 are inserted near a stomach to a small intestine of a subject is described in each example below, but a situation in which the endoscope system of the present invention is applicable is not limited to such a case.

Example 1

FIG. 5 is a graph illustrating the state of a bending stiffness change in Example 1. In Example 1, the bending stiffness change portion 80 is provided over the full range of the above-mentioned projection region 70 (the region of the flexible portion 36 that projects from the distal end opening 56 of the overtube 50 in a state where the insertion portion 12 is located in the distal end position in a movable range with respect to the overtube 50, that is, in a state where the insertion portion 12 is moved until the boot 15 abuts on the inner edge of the proximal end opening 58). Specifically, as illustrated in FIG. 5, a first position P1 in which the bending stiffness begins to increase is located at a position apart by 100 mm from the distal end of the insertion portion 12 (the distal end surface of the distal-end hard portion 40), a second position P2 in which the increase in the bending stiffness ends is located at a position apart by 500 mm from the distal end, and the length of the bending stiffness change portion 80 is 400 m.

Thus, in Example 1, the length of the bending stiffness change portion 80 and the length of the projection region 70 are equal, and, a part of the flexible portion 36 in the proximal end side rather than the bending stiffness change portion 80, is entirely covered with the overtube 50.

Moreover, in Example 1, the bending stiffness in the bending stiffness change portion 80 uniformly increases from the first position P1 toward the second position P2 (the increasing rate of the bending stiffness is constant). Further, when the bending stiffness in the first position P1 is assumed to be 1, the bending stiffness (relative ratio) in the second position P2 and a position on the proximal end side from the second position P2 is assumed to be 2 or more. If the insertion portion 12 and the overtube 50 are inserted deeply (on the small intestine side) than the stomach of a subject, since there are a small bending portion, and so on, after the stomach and the distal end portion of the insertion portion 12 is less likely to move forward, the flexible portion 36 is likely to warp before the distal end portion (proximal end side), but, by setting the bending stiffness in a portion covered with the overtube 50 to be more than twice as large as the bending stiffness of the minimum bending stiffness portion (first position P1) in Example 1, it is possible to prevent the warpage (deflection) on the near side and facilitate the insertion.

Here, the bending stiffness change illustrated in FIG. 5 can be realized by changing the thickness of resin layers with different bending stiffness or the mixing ratio of resins in the shell 37E of the flexible portion 36 as described above.

Example 2

FIG. 6 is a graph illustrating the state of a bending stiffness change in Example 2. In Example 2, the bending stiffness uniform portion 82 is provided in a range of 100 mm from the connection portion between the bending portion 38 and the flexible portion 36. In this bending stiffness uniform portion 82, the bending stiffness is constant (the bending stiffness is the least in the flexible portion 36) along the longitudinal axis direction of the flexible portion 36 (the X direction in FIG. 3). The most-proximal end-side position of the bending stiffness uniform portion 82 is a first position P1 in Example 2, the bending stiffness change portion 80 is provided in a range of 300 mm from this first position P1 to second position P2 on the proximal end side, and the bending stiffness gradually increases. The proximal end side than the second position P2 is covered with the overtube 50. Here, in a similar way to Example 1, when the bending stiffness in the first position P1 is assumed to be 1, the bending stiffness (relative ratio) in the second position P2 is assumed to be 2 or more.

By providing the bending stiffness uniform portion 82 on the side of the bending portion 38 and lengthening the portion having the minimum bending stiffness like Example 2, even if the insertion portion 12 is pressed in a state where the bent bending portion 38 contacts with an intestinal wall (the state illustrated in FIG. 7A) when the insertion portion 12 is inserted into a subject as illustrated in FIGS. 7A and 7B, the bending stiffness uniform portion 82 with the minimum bending stiffness is bent by this press power and absorbs the press power (the state illustrated in FIG. 7B), and it is possible to mitigate a load to the intestinal wall.

Example 3

FIG. 8 is a graph illustrating the state of a bending stiffness change in Example 3. In Example 3, the bending stiffness change portion 80 is provided on the further proximal end side than the projection region 70 in addition to the full range of the above-mentioned the projection region 70. Specifically, as illustrated in FIG. 8, a first position P1 in which bending stiffness begins to increase is located at a position apart by 100 mm from the distal end of the insertion portion 12, and an increase in the bending stiffness ends at a third position P3 (third position) (apart by 600 mm from the distal end) on the proximal end side further apart by 100 mm from a second position P2, over the second position P2 (the projection region 70 ends here) that is a position apart by 500 mm from the distal end. In a similar way to Examples 1 and 2, when the bending stiffness in the first position P1 is assumed to be 1, the bending stiffness (relative ratio) in the third position P3 is assumed to be 2 or more.

Thus, the length of the bending stiffness change portion 80 is 500 m in Example 3. That is, even in a region covered with the overtube 50 of the flexible portion 36, the bending stiffness change portion 80 is provided from the second position P2 to the third position P3. Here, it is assumed that a distance from the second position P2 to the third position P3 be 100 mm in Example 3, but the distance from the second position P2 to the third position P3 may be assumed to be other values than this (for example, a range equal to or greater than 100 mm and equal to or less than 200 mm).

By forming the bending stiffness change portion 80 up to the third position P3 like Example 3, a change in the curvature range of the insertion portion 12 in the position in which the change in the bending stiffness ends can be absorbed in the range covered with the overtube 50.

Here, even in Example 3, the bending stiffness uniform portion 82 (which is a portion with the minimum bending stiffness) may be provided in the distal end portion of the flexible portion 36 in a similar way to Example 2. FIG. 9 illustrates an example of a bending stiffness change in this case.

Example 4

FIG. 10 is a graph illustrating the state of a bending stiffness change in Example 4. As illustrated in FIG. 10, the bending stiffness change portion 80 ends on the distal end side than the projection region 70 in Example 4. Specifically, a first position P1 in which bending stiffness begins to increase is located at a position apart by 100 mm from the distal end of the insertion portion 12, and an increase in the bending stiffness ends in a second position P2 that is located at a position apart by 400 mm from the distal end. In a similar way to Examples 1 to 3, when the bending stiffness in the first position P1 is assumed to be 1, the bending stiffness in the second position P2 is set to be 2 or more. Thus, the length of the bending stiffness change portion 80 is 300 mm in Example 4. The range from the first position P1 up to a position apart by 100 mm from the second position P2 on the further proximal end side is the projection region 70. Here, the bending stiffness is constant on the proximal end side from the second position P2.

FIG. 11 is a diagram illustrating a state in which the insertion portion 12 having the bending stiffness change portion 80 in Example 4 and the overtube 50 are inserted into the stomach portion of a subject whose stomach completely remains. As illustrated in FIG. 11, when the distal end portion of the insertion portion 12 (shown by the solid line in FIG. 11) is in anastomosis portion PA, the insertion portion 12 is likely to warp near a position PB (a position apart by about 400 mm to 600 mm from the anastomosis portion PA) of the stomach inside the body and the distal end may not move forward (on the small intestines side). By forming the bending stiffness change portion 80 like Example 4 and increasing the bending stiffness of the insertion portion 12 inside the stomach, it is possible to prevent the deflection (warpage) of the insertion portion 12 inside the stomach and make the distal end portion move forward easily.

Here, in a similar way to Examples 1 to 3, when the bending stiffness in the first position P1 is assumed to be 1, the bending stiffness in the second position P2 is set to be 2 or more.

<Relationship Between Bending Stiffness Variation Amount in Bending Stiffness Change Portion and Maximum Bending Stiffness of Overtube>

FIGS. 12A and 12B are graphs illustrating examples of the relationship between the bending stiffness variation amount in a bending stiffness change portion and the maximum bending stiffness of the overtube in the present invention. In the present invention, it is effective when the difference between the maximum bending stiffness and the minimum bending stiffness in the bending stiffness change portion 80 is made larger than half of the maximum bending stiffness of the overtube 50 as illustrated in FIGS. 12A and 12B.

Specifically, as illustrated in FIG. 12A, when the value of the bending stiffness of the overtube 50 alone is assumed to be C and the values of the bending stiffness in the bending stiffness change portion 80 are assumed to be A (which is the value in the first position P1) and B (which is the value in the second position P2) (where A, B and C are greater than 0 and B is greater than A), the values A, B and C are set to establish $(B-A) > \{(1/2) \times C\}$. In this case, the total bending stiffness of the insertion portion 12 and the overtube 50 is as illustrated in FIG. 12B.

Here, the relationship of such bending stiffness can be adopted in any of Examples 1 to 4 mentioned above.

As described above, in the endoscope system 100 according to the present invention, it is possible to secure appropriate bending stiffness of an insertion portion while maintaining the slide length of the insertion portion.

<Other Inventions>

Next, endoscope systems as another invention of the present invention are described. A region (the bending stiffness change portion 80) in which bending stiffness changes is provided in at least a part of the projection region 70 in Examples 1 to 4 of the above-mentioned present invention. In the other invention, a bending stiffness change portion 83 is provided in a portion (covered region) in which the flexible portion 36 is covered with the overtube 50 in a state where the bending stiffness is assumed to be constant (minimum bending stiffness portion) in the projection region 70 and the insertion portion 12 is slidden (moved) until the boot 15 abuts on the overtube 50 (that is, until the insertion portion 12 is located in the distal end position in a movable range with respect to the overtube 50).

<Configuration of Endoscope System>

Since the configuration of the endoscope system according to the other invention is similar to the configuration illustrated in FIGS. 1 and 2 except for the bending stiffness change portion 83 shown below, the same reference numerals are assigned to the same components and detailed explanation thereof is omitted.

FIG. 13 is a diagram illustrating the bending stiffness of the flexible portion 36 in the other invention. As illustrated in FIG. 13, in the other invention, the distal end position of the projection region 70 is apart by 100 mm from the distal end of the insertion portion 12, and the length of the projection region 70 is 400 mm (up to 500 mm from the distal end of the insertion portion 12). Further, in a region in which the flexible portion 36 is covered with the overtube 50, a portion (minimum bending stiffness portion) from the most proximal end portion of the projection region 70 up to a first position P1 apart by 200 mm further toward the proximal end side (up to 700 mm from the distal end of the insertion portion 12) has a constant bending stiffness. The range from this first position P1 to a second position P2 on the further proximal end side (apart by 900 mm from the distal end of the insertion portion 12) is the bending stiffness change portion 83 in which the bending stiffness increases.

Here, the length of a covered region 72 (a range in which the flexible portion 36 is covered with the overtube 50) is assumed to be 200 mm in the example of FIG. 13, but the length of the covered region 72 may be changed within a range of 200 mm to 300 mm. Moreover, the length of the bending stiffness change portion 83 may be changed within a range of 200 to 300 mm.

Moreover, in the other invention, a change in the bending stiffness in the bending stiffness change portion 83 can be realized by changing the thickness of resin layers with different hardness or by changing the mixing ratio of resins in a similar way to FIGS. 2 and 4 and description in association with these figures.

In the other invention, too, when the bending stiffness in a minimum bending stiffness portion is assumed to be 1, it is preferable that the bending stiffness (relative ratio) on the proximal end side from second position P2 is set to be 2 or more. Moreover, it is preferable that the relationship between the bending stiffness of the flexible portion 36 and the bending stiffness of the overtube 50 is also set similarly to FIGS. 12A and 12B.

FIG. 14 is a diagram illustrating a state in which the insertion portion 12 and the overtube 50 of the endoscope system 100 according to the other invention are inserted into a subject whose stomach is completely removed. For such the subject, in the endoscope system 100 according to the other invention, by setting the entire portion (about 600 mm at maximum) inserted after the Y-leg (an anastomotic region between the small intestine and the duodenum) shown by reference numeral PY in FIG. 14 to be a minimum bending stiffness portion (with a length of 700 mm in the above-mentioned example), it is possible to reduce a load due to insertion from the Y-leg to the duodenum side.

In the endoscope system according to the other inventions, too, it is possible to secure appropriate bending stiffness of the insertion portion while maintaining the slide length of the insertion portion in a similar way to the previous description of the present invention.

Moreover, the present invention and the other invention are not limited to the above-mentioned embodiments, and various changes can be made without departing from the scope of each invention.

What is claimed is:

1. An endoscope system comprising:
   an endoscope configured to include an insertion portion to be inserted into a body and an operation portion connected with a proximal end side of the insertion portion, where the insertion portion includes a distal-end hard portion, a bending portion connected with a proximal end side of the distal-end hard portion, and a flexible portion connected with a proximal end side of the bending portion; and
   an insertion assisting tool configured to i) be inserted into the body together with the insertion portion such that the insertion assisting tool and the insertion portion are slidable with respect to one another in the body and ii) include a tube body with a distal end opening and a proximal end opening, the tube body including an insertion path into which the insertion portion is inserted from the proximal end opening, where the insertion portion is movable forward and backward in a longitudinal axis direction of the tube body and the tube body is formed to have a length in which at least a part of the flexible portion projects from the distal end opening when the insertion portion is located in a distal end position in a movable range with respect to the tube body, wherein:
   the flexible portion includes a projection region which projects from the distal end opening when the insertion portion is located in the distal end position in the movable range with respect to the tube body;
   the projection region includes a bending stiffness change portion in which a bending stiffness increases from a first position toward a second position, wherein the first position is nearer to a distal end position of the projection region than to a proximal end position of the projection region, or is the distal end position of the projection region, and the second position is the proximal end position of the projection region,
   the bending stiffness change portion is formed from the first position to the second position and is further formed up to a third position on a proximal end side of the projection region in the flexible portion, wherein the bending stiffness increases continuously from the second position to the third position,
   the flexible portion also includes a first bending stiffness uniform portion on a proximal end side of the third position, wherein the first bending stiffness uniform portion has a constant bending stiffness along a longitudinal axis direction of the flexible portion, and
   a difference between a maximum bending stiffness and a minimum bending stiffness of the bending stiffness change portion is greater than a half of a bending stiffness of a maximum bending stiffness portion in the tube body and is smaller than the bending stiffness of the maximum bending stiffness portion in the tube body.

2. The endoscope system according to claim 1, wherein the first position is the distal end position of the projection region.

3. The endoscope system according to claim 1, wherein the projection region includes a second bending stiffness uniform portion on a distal end side of the first position, and the second bending stiffness uniform portion has a constant bending stiffness along the longitudinal axis direction of the flexible portion.

4. The endoscope system according to claim 1, wherein a maximum bending stiffness of the bending stiffness change portion is twice or more as large as a minimum bending stiffness.

5. An endoscope system comprising:
   an endoscope configured to include an insertion portion to be inserted into a body and an operation portion connected with a proximal end side of the insertion portion, where the insertion portion includes a distal-end hard portion, a bending portion connected with a proximal end side of the distal-end hard portion, and a flexible portion connected with a proximal end side of the bending portion; and
   an insertion assisting tool configured to i) be inserted into the body together with the insertion portion such that the insertion assisting tool and the insertion portion are slidable with respect to one another in the body and ii) include a tube body with a distal end opening and a proximal end opening, the tube body including an insertion path into which the insertion portion is inserted from the proximal end opening, where the insertion portion is movable forward and backward in a longitudinal axis direction of the tube body, wherein:
   the insertion assisting tool includes an abutting portion which abuts on the endoscope on a proximal end side of the tube body, and the tube body is formed to have a length in which at least a part of the flexible portion projects from the distal end opening when the endoscope abuts on the abutting portion;
   the flexible portion includes a projection region which projects from the distal end opening when the endoscope abuts on the abutting portion;

the projection region includes a bending stiffness change portion in which a bending stiffness increases from a first position toward a second position, wherein the first position is nearer to a distal end position of the projection region than to a proximal end position of the projection region, or is the distal end position of the projection region, and the second position is the proximal end position of the projection region, the bending stiffness change portion is formed from the first position to the second position and is further formed up to a third position on a proximal end side of the projection region in the flexible portion, wherein the bending stiffness increases continuously from the second position to the third position, the flexible portion also includes a first bending stiffness uniform portion on a proximal end side of the third position, wherein the first bending stiffness uniform portion has a constant bending stiffness along a longitudinal axis direction of the flexible portion, a difference between a maximum bending stiffness and a minimum bending stiffness of the bending stiffness change portion is greater than a half of a bending stiffness of a maximum bending stiffness portion in the tube body and is smaller than the bending stiffness of the maximum bending stiffness portion in the tube body.

6. The endoscope system according to claim 5, wherein the first position is the distal end position of the projection region.

7. The endoscope system according to claim 5, wherein the projection region includes a second bending stiffness uniform portion on a distal end side of the first position, and the second bending stiffness uniform portion has a constant bending stiffness along the longitudinal axis direction of the flexible portion.

8. The endoscope system according to claim 5, wherein a maximum bending stiffness of the bending stiffness change portion is twice or more as large as a minimum bending stiffness.

9. The endoscope system according to claim 1, wherein the insertion portion of the endoscope further includes a first balloon attached to an outer periphery of the bending portion, and the insertion assisting tool further includes a second balloon attached to an outer peripheral surface at a distal end portion of the tube body.

10. The endoscope system according to claim 5, wherein the insertion portion of the endoscope further includes a first balloon attached to an outer periphery of the bending portion, and the insertion assisting tool further includes a second balloon attached to an outer peripheral surface at a distal end portion of the tube body.

\* \* \* \* \*